Figure 1:
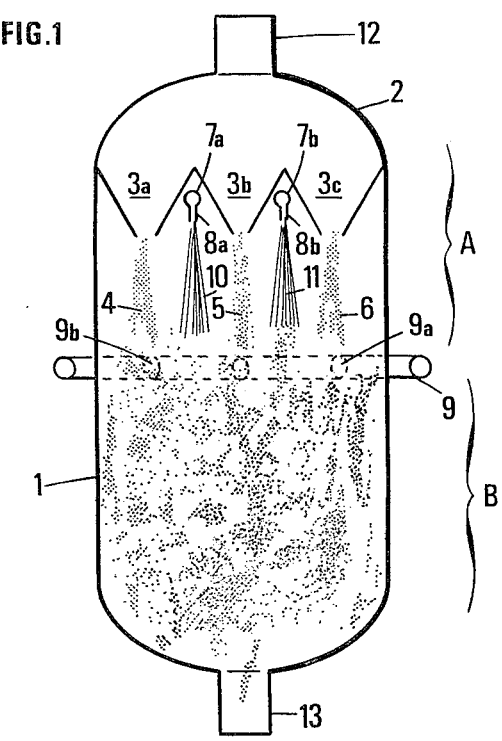

United States Patent [19]

Busson et al.

[11] Patent Number: 4,472,264
[45] Date of Patent: Sep. 18, 1984

[54] PROCESS FOR CONVERTING SOLID CARBONACEOUS MATERIALS TO METHANE

[75] Inventors: Christian Busson, Tassin La Demi-Lune; Jacques Alagy, Charbonnieres; Jean-Paul Euzen, Dardilly; Pierre Galtier, Vienne-Estressin, all of France

[73] Assignee: Institut Francais du Petrole, Rueil-Malmaison, France

[21] Appl. No.: 461,413

[22] Filed: Jan. 27, 1983

[30] Foreign Application Priority Data

Jan. 27, 1982 [FR] France ............................ 82 01388

[51] Int. Cl.$^3$ ..................... C10G 1/00; C10G 3/68
[52] U.S. Cl. ............................. 208/8 LE; 208/8 R; 48/201
[58] Field of Search ............... 208/8 LE, 8 R; 48/201

[56] References Cited

U.S. PATENT DOCUMENTS

| | | | |
|---|---|---|---|
| 3,817,723 | 6/1974 | Donath | 208/8 R |
| 3,855,070 | 12/1974 | Squires | 208/8 R X |
| 3,960,700 | 6/1976 | Rosen et al. | 208/8 R |
| 4,048,053 | 9/1977 | Greene | 208/8 R |
| 4,075,079 | 2/1978 | Lang | 208/8 LE |
| 4,097,360 | 6/1978 | Sack | 208/8 R |
| 4,101,412 | 7/1978 | Choi | 208/8 R |
| 4,162,959 | 7/1979 | Durai-Swany | 208/8 R |
| 4,206,032 | 6/1980 | Friedman et al. | 208/8 R |
| 4,263,124 | 4/1981 | Wickstom et al. | 208/8 R |
| 4,324,638 | 4/1982 | Durai-Swany | 208/8 R |
| 4,366,043 | 12/1982 | Chokhanov et al. | 208/8 R |

*Primary Examiner*—Delbert E. Gantz
*Assistant Examiner*—William G. Wright
*Attorney, Agent, or Firm*—Millen & White

[57] ABSTRACT

Process for converting solid carbonaceous materials to methane, comprising (a) converting the carbonaceous material by means of a reducing gas at 300°–500° C. to a semi-oily phase adapted to be pumped and atomized, (b) heating falling droplets of said semi-oily phase to a temperature of 700°–1600° C. with hot solid particles in downward jets in the presence of reducing gas, under a presssure above 20 bars, (c) separating the solid particles of large size (d), heating them and feeding them back to step (b), (e) cooling the remaining fraction consisting of gas and solid particles of small size by means of a cold reducing gas and separating methane therefrom, and (f) treating the remaining solid phase of fine particles with oxygen and steam to produce a reducing gas fed back to steps (a) and (b).

13 Claims, 2 Drawing Figures

PROCESS FOR CONVERTING SOLID CARBONACEOUS MATERIALS TO METHANE

BACKGROUND OF THE INVENTION

Direct methanation of coal, in order to produce synthesis natural gas, has been the object of much effort for several years. For example, a process is known wherein powdered coal is reacted with overheated hydrogen (see for example U.S. Pat. Nos. 3,960,700 and 4,206,032).

These processes suffer from the disadvantages due to the difficulty of uniformly distributing the powdered solid coal into the numerous nozzles required for operating the process on an industrial scale and to the high hydrogen consumption.

According to another proposal, particles of coal or pitch are used as heat carrier and as reactant for producing a hydrogenating gas.

The U.S. Pat. No. 3,855,070 describes a process of this type making use of the larger coke particles as reactant for producing hydrogenating gas: these particles are treated with a mixture of air or oxygen and steam. The resultant gas is then burnt in contact with fine particles of coke, so as to heat them, the heated fine particles being then fed to the coal pyrolysis zone where they supply the required heat. This process suffers from disadvantages inasmuch as it is particularly difficult to completely gasify large particles in view of the limited diffusion therethrough.

According to another proposal (U.S. Pat. No. 4,162,959), the coke discharged from the pyrolysis zone is successively subjected to a partial combustion, destined to increase its temperature, then to a treatment with steam destined to produce the hydrogen necessary for the reaction; the residual coke is then fed to the pyrolysis zone to supply the heat required for the reaction. This process results in a certain simplification of the technique of U.S. Pat. No. 3,855,070, but hs some defects. As a matter of fact, the treatment with steam being endothermic, the solid issued from this treatment cannot be brought to a very high temperature, for example of 1000° C., which is detrimental to a good development of the pyrolysis.

OBJECTS OF THE INVENTION

The process of the invention has for object to cope with the defects of the prior processes. Particularly, it has for object to favor cracking reactions leading to the formation of hydrocarbons and a concomitantly reduced coking reaction, while providing for a better dispersion of the carbonaceous material in the pyrolysis chamber, a quick increase in temperature of the carbonaceous material in said zone and an improved thermal transfer by radiation rather than by conduction and convention.

SUMMARY OF THE INVENTION

These various advantages are obtained as follows:

a. In a first step, the powdered solid carbonaceous material is treated with a heavy oil containing aromatic hydrocarbons and with a hydrogen-containing reducing gas, at a temperature from 300° to 500° C. under a pressure of at least 20 bars, so as to convert at least a part of the carbonaceous material to an oily phase, so that the resultant mixture can be pumped, transported and atomized. The so-obtained mixture is called semi-liquefied material.

b. In a second step, the semi-liquefied material is introduced into an empty chamber under an atmosphere of a hydrogen-containing reducing gas in the form of a plurality of downward jets of droplets and hot solid particles of a heat carrying material of a relatively large grain size are introduced into the same chamber as downwardly directed jets, parallel to the jets of droplets but without substantial direct contact therewith, at least in the upper part of the chamber. The temperature and the flow rate of the jets are so regulated as to maintain an average temperature from 700° to 1600° C. within said chamber, the pressure in said chamber being at least 20 bars.

c. In a third step, the effluent from step (b) is separated into a fraction of solid particles of relatively large grain size and a fraction containing gases and carbonaceous solid particles of relative smaller grain size, without substantially cooling said effluent of step (b).

d. In a fourth step, at least a portion of the fraction of solid particles of relatively large grain size is heated and fed back to step (b) as heat carrier.

e. In a fifth step, the fraction containing gases and carbonaceous materials of smaller grain size is cooled down by means of a relatively cool hydrogen-containing reducing gas and this fraction is then separated into a fraction of relatively fine carbonaceous particles and a gas phase fraction.

f. At least a portion of the fraction of relatively fine particles obtained in step (e) is treated with oxygen and steam to produce a hydrogen-containing reducing gas, and at least a portion of said gas is fed to step (a) and at least another portion to step (b).

DETAILED DISCUSSION

By solid material of relatively large grain size, is meant particles of an inorganic material withstanding heat, for example alumina, silica, an aluminate, a silicate or, preferably, coke. The average grain size is at least 25 $\mu$m, for example from 50 to 100 $\mu$m. By coke, is meant coal coke or oil coke properly, as well as pitch.

The particles of small grain size have an average grain size smaller than 25 $\mu$m, for example from 5 to 15 $\mu$m. They are, at least partly, formed of coke.

The reducing gas may be relatively pure hydrogen or a synthesis gas containing both hydrogen and carbon monoxide.

The semi-liquefied material obtained in step (a) may contain solids in suspension and have a relatively high viscosity or, on the contrary, a relative fluidity.

The essential condition is that it can be pumped, transported and atomized.

The heavy hydrocarbon oil used in step (a) may be of extraneous origin; in this case highly aromatic oils are preferred (>20% of aromatics by weight; Eb>300° C.); later in the process, this oil advantageously consists of a recycled fraction of the oily phase formed in the same step.

The solid carbonaceous material subjected to the process is used as powder; a fine grain size is preferred, for example at least 80% of particles of a size smaller than 70 $\mu$m. This carbonaceous material is for example coal, lignite or any other form of fossil coal.

It is unnecessary to convert the solid carbonaceous material to a completely liquid phase during the first step; it is preferred to limit this step to a softening with formation of a liquid phase. The semi-liquefied material is introduced into a pyrolysis chamber in atomized form, for example through an injector with steam as driving gas. There is so obtained fine droplets of a diameter as small as 20 μm.

The residence time of the droplets in the pyrolysis chamber is from about 1 to 500 milliseconds, preferably from 1 to 50 milliseconds. The particular heating mode of the jets of droplets by parallel jets of hot solids makes it possible to increase very quickly the temperature, thus favoring the cracking reaction to the prejudice of the coking reaction. The solids are admitted at a very high temperature, about 800° to 1600° C., preferably 1100° to 1400° C.

According to a preferred embodiment, each jet of droplets is surrounded by a curtain of hot solid particles, as shown in FIG. 1.

In order to obtain the highest possible heat exchange, it is preferred to multiply the number of jets of solids and of jets of semi-liquefied material for a given capacity. It is thus preferred to make use of a pyrolysis chamber comprising a large number of nozzles for injecting the semi-liquefied material, each of them injecting a beam of droplets surrounded by a close curtain of solid particles in gravitational flow. It is important that the size of the droplets be as small as possible in order that the heat exchange not be slowed down by the thermal diffusion from the outside to the inside of the droplet. FIG. 1 shows an embodiment of this chamber with alternate atomization nozzles and curtains of solid particles.

Although the heat exchange is essentially effected by radiation, the participation in the heat transfer of other forms of heat exchange, by conduction and/or convection, is by no means excluded. However, the heat exchange by radiation is still preferred since, at least during the first milliseconds, agglomerates are liable to be formed in case of direct contact between the droplets and the solid particles.

By adapting the respective flow rates of hot solid carrier and of the semi-liquefied material, the temperature of the latter is brought to about 700° C. or above in a few milliseconds, preferably less than 500 milliseconds, taking account of the heat required for the cracking and the evaporation of the volatile materials either present initially or formed by cracking.

From the moment when the residual unvolatilized portion of the semi-liquefied material droplets reaches about 700° C., the methanation reaction will be enhanced and will apply to the hydrogenolysis of volatile materials as well as to that of materials still liquid or even of the solid particles which are the ultimate residue of the droplets.

In order to control this highly exothermic methanation reaction, it is advantageous to inject cold reducing gas in the intermediary portion of the methanation reactor. The solids and particularly the coke, used as heat carrier, remain inert with respect to hydrogen under the indicated operating conditions. The cokefied portion of the semi-liquefied material will come in addition to the coke heat carrier. In the second part of the reactor, the internal heat transfer being no longer necessary and the dangers of agglomeration being averted, the solid heat carrier and the different reactants and reaction products may become admixed by the swirling of the medium.

FIG. 1 is a cross-sectional view of the pyrolysis furnace used in the claimed invention.

FIG. 1 is a cross-sectional view of the pyrolysis furnace 1 along a vertical plane. This furnace comprises a zone 2 for receiving hot coke particles conveyed from a furnace through line 12. These particles are supplied through orifices such as 3a, 3b, 3c so as to form curtains (4, 5, 6) of particles. Each curtain is interposed between jets (10, 11) of atomized liquid (semi-liquefied material), issued from a series of injectors such as 8a and 8b, placed on feed lines such as 7a, 7b.

The reducing gas required for controlling the methanation temperature is injected through a series of nozzles (9a, 9b) on the concentric external line 9. This series of cold reducing gas injection nozzles defines the limit between an upper zone A where it is preferred to reduce the turbulence and a lower zone B. The products are discharged through line 13 and conveyed towards a first cyclone. The residence time in the non-turbulent zone A is preferably from 1 to 50 milliseconds and in the turbulent zone B preferably from 20 to 480 milliseconds.

At the outlet of the methanation reactor, the mixture of solid and gaseous products is conveyed to a phase separation device formed of a cyclone assembly. In a first hot operated cyclone the major part of the large size particles is recovered. At the output of said first cyclone, the gaseous phase driving therewith the smaller "fine" particles is cooled by injection of hydrogen-containing cold gas and the whole is fed to the input of a second cyclone wherefrom is recovered, on the one hand, the methane containing gas and, on the other hand, the small particles. The cooling brings the temperature preferably below 400° C.

The flow of small coke particles is conveyed to an oxyvapogasification reactor of conventional type (step g) so as to produce a gas containing $CO + H_2$; this reactor is optionally followed with a CO conversion reactor for producing hydrogen. When the amount of small coke particles issued from the second cyclone is insufficient to produce a sufficient amount of hydrogen or of $CO + H_2$ mixture required for the process, a portion of the flow of the large particles issued from the first hot cyclone is also fed to the oxyvapogasification reactor. The production of hydrogen and of synthesis gas is used to satisfy the needs of the process but an additional production may be considered, in view of feeding for example a methanol production unit.

The main flow of large particles, issued from the first hot cyclone, is conveyed to a heating furnace where it is brought to about 1000° to 1600° C. This furnace is preferably formed of an enclosure equipped on its periphery with radiant burners with flat flame. In front of the burners, the solid falls as a dropping curtain. The radiant burners of the preheating furnace are preferably fed with a portion of the semi-liquefied material issued from the first step and with oxygen or air, although other combustion agents may also be used.

Figure 2:
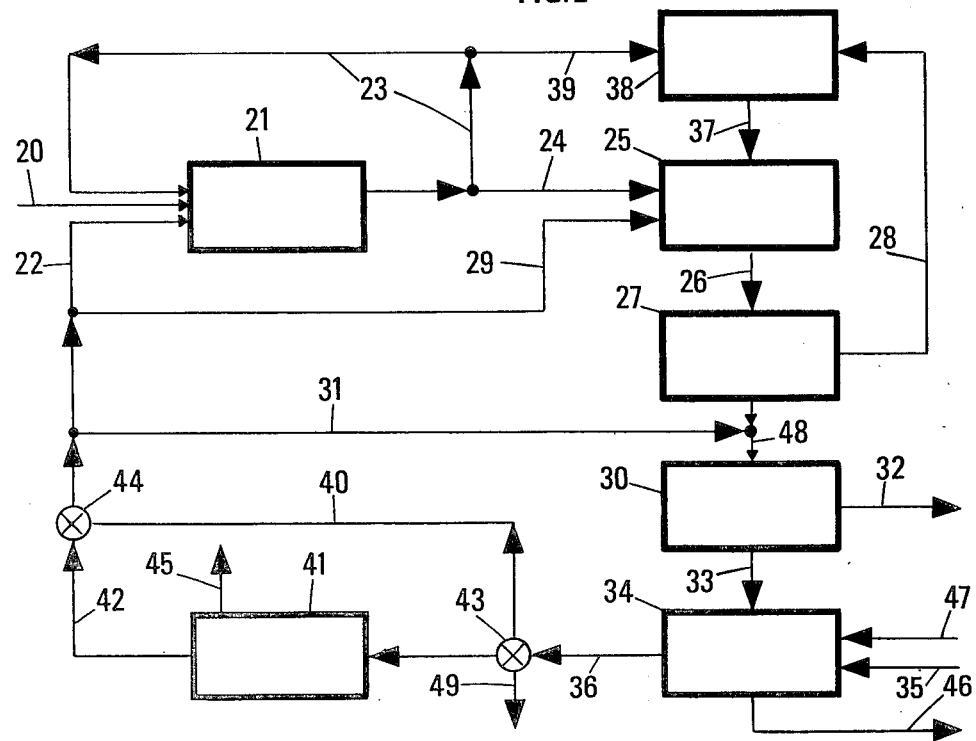

At the bottom of the furnace the heated solid is conveyed to the methanation reactor. According to a preferred embodiment, the methanation reactor is located below the heater. In FIG. 2, the whole diagram of the apparatus for carrying out the invention is shown.

FIG. 2 is a block diagram of the claimed invention.

In FIG. 2, coal is introduced through line 20 into the semi-liquefaction reactor 21; this reactor is also fed with a hydrogen-containing reducing gas (line 22) and with a hydrocarbon liquid fraction which may consist of an aromatic heavy oil or may, at least partly, consist of the recycled semi-liquefied material (line 23). The obtained semi-liquefied material is fed through line 24 to the methanation reactor 25. The latter is also fed with a reducing gas, hydrogen or a hydrogen+carbon monoxide mixture (line 29), as well as with coke particles at high temperature, issuing through line 37 from furnace 38. The latter is heated by combustion with a fuel of any type, this fuel being optionally formed of any heavy or residual oil or, advantageously, of a portion of the semi-liquefied materail (line 39). The effluent from reactor 25 is fed through line 26 to cyclone 27 for separating the larger solid particles. The latter are then fed through line 28 to furnace 38 when they are heated and then used as heat carrier in reactor 25. The temperature of cyclone 27 is substantially the same as that of furnace 25; the cyclone may thus be placed directly in the furnace 25, at the output thereof. The gas and the smaller solid particles are fed through line 48 to a second cyclone 30. Relatively cold hydrogenating gas (fed through line 31) is previously admixed thereto. There is thus separated gas (line 32) and relatively fine solid particles (line 33). The gas contains the desired methane as well as heavier hydrocarbons, for example ethane, light aromatic hydrocarbons (benzene, toluene, xylenes) and optionally heavier hydrocarbons; less desirable gaseous products such as $H_2S$, CO and $CO_2$, are also present. This gas may be fractionated and purified in a known manner.

The carbonaceous solid materials from line 33 are fed to the gasification reactor 34. The latter is of conventional type and receives oxygen and steam (through line 35) and eventually additional coal (line 47). The reaction between the carbonaceous particles, oxygen and steam generates a gas containing CO, $CO_2$ and $H_2$ (line 36). This gas may be directly supplied, through lines 36 and 40, to lines 22, 29 and/or 31. It may also be treated in unit 41 for converting CO to $CO_2$ and removing the latter. The obtained relatively pure hydrogen is then fed through line 42 to lines 22, 29 and 31. Through valves 43 and 44, the desired conveying path is selected. Carbon dioxide is discharged (45). The gasification reactor also comprises a line for discharging ashes (line 46). Line 49 is provided for withdrawing an eventual reducing gas excess.

The carbonaceous material subjected to the process may be coal, lignite or another source of solid carbonaceous material.

EXAMPLE

Coal issued from the Lorraine basin (France), having an ash content of 6.1% of weight and a content of volatile materials of 36.1% by weight, is subjected to the treatment.

This coal, in powder form (more than 70% of particles of a size smaller than 80 μm) is treated at 400° C. and 90 bars, for 90 minutes, by means of a hydrocarbon fraction ($bp_{760}$=350°-500° C.; aromatic content: 52% by weight). The atmosphere consists of 95% hydrogen.

There is so obtained a transportable material which is injected in the methanation reactor, as jets of droplets parallel to jets of solid carbonaceous particles (size of about 25 to 100 μm) introduced at 1400° C.

The average temperature is 1050° C., the pressure 80 bars and the residence time 10 milliseconds (zone A) and 200 milliseconds (zone B). The atmosphere consists of 95% of hydrogen. Additional hydrogen is injected between zones A and B.

The effluent is fed to a cyclone, without substantial cooling: the carbonaceous solid particles (about 25–100 μm) are recovered and fed to a furnace, in order to be recycled at 1400° C. The other products are quickly cooled down to 300° C. by injection of cold hydrogen and fed to a cyclone to separate the fine carbonaceous particles (<25 μm) from the methane containing gas, which constitutes the final product of the process.

The fine carbonaceous particles are supplied to a reactor fed with oxygen and steam, so as to produce the reducing gas ($H_2$) required for the process.

Per each ton of coal, there is thus recovered 582 $m^3$ of methane, 84 kg of BTX (benzene, toluene and xylenes mixture) and 40 kg of other light hydrocarbons.

What is claimed is:

1. A process for converting a solid carbonaceous material to methane, comprising the steps of:
   (a) reacting a mixture of a powdered solid carbonaceous material and a heavy hydrocarbon oil containing aromatic hydrocarbons with a hydrogen-containing reducing gas at a temperature of 300°–500° C. and under a pressure of at least 20 bars, so as to convert at least a portion of the carbonaceous material to an oily phase, to produce resultant pumpable, transportable and atomizable semi-liquefied material;
   (b) introducing at least a portion of said semi-liquefied material, and hot solid particles of a heat carrier material being of a relatively large particle size, into an upper, non-turbulent zone of a methanation reactor, in a hydrogen-containing reducing gas atmosphere, said semi-liquefied material being introduced in the form of a plurality of jets of downwardly directed droplets, and said solid particles being introduced in the form of downwardly directed jets, parallel to the jets of droplets but without substantial direct contact therewith in said upper, non-turbulent zone, the residence time of said droplets in said non-turbulent zone being 1–50 milliseconds; and admixing said droplets and said solid particles so that they flow in direct contact with one another in a lower, turbulent zone of said reactor, the residence time in said turbulent zone being 20–480 milliseconds; the temperature and the flow rate of the jets being so adjusted as to maintain an average temperature of 700°–1600° C. in said reactor, the pressure in said reactor being at least 20 bars;
   (c) separating the effluent from step (b) into a fraction of solid particles of relatively large size, and a fraction comprising gas and carbonaceous solid particles of relatively smaller particle size, without substantially cooling said effluent from step (b);
   (d) heating at least a portion of the solid particles fraction of relatively large particle size from step (c), and feeding the heated particles to step (b) as said heat carrier;
   (e) contacting the fraction containing gas and carbonaceous particles of smaller grain size from step (c) with a relatively cool hydrogen-containing reducing gas, to cool said fraction, and then separating said fraction and separately recovering a fraction of relatively small carbonaceous particles, and a methane-containing gaseous phase fraction; and
   (f) treating with oxygen and steam at least a portion of the fraction of relatively small particles obtained from step (e), to produce a hydrogen-containing reducing gas, and supplying at least a portion of said gas to step (a), and at least another portion to step (b).

2. A process according to claim 1, wherein, in step (b), the jets of solid particles form curtains separating a series of jets of said droplets.

3. A process according to claim 1, wherein, in step (b), the inlet temperature of the hot solid particles is from 800° to 1600° C.

4. A process according to claim 3, wherein, said, the inlet temperature of the hot solid particles is from 1100° to 1400° C.

5. A process according to claim 1, wherein, in step (a), the heavy hydrocarbon oil consists at least partly of a recycled portion of the semi-liquefied material.

6. A process according to claim 1, wherein the reducing gas produced in step (f) is treated to remove therefrom at least the major part of the carbon oxides contained therein, so as to feed steps (a) and (b) with a gas of higher hydrogen content.

7. A process according to claim 1, wherein the heating of the solid particles in step (d) is effected by combustion of a portion of the semi-liquefied material obtained in step (a).

8. A process according to claim 1, wherein the solid particles introduced in step (b) are coke particles.

9. A process according to claim 1, wherein the temperature of step (b) is controlled by introducing a relatively cool hydrogen containing gas at an intermediate point of said chamber.

10. A process according to claim 1, wherein said particles of heat carrier material of relatively large particle size have an average grain size of at least 25 $\mu$m, and said particles of relatively smaller particle size have an average grain size of less than 25 $\mu$m.

11. A process according to claim 10, wherein said particles of relatively large particles size have an average grain size of 50–100 $\mu$m, and said particles of relatively smaller particle size have an average grain size of 5–15 $\mu$m.

12. A process according to claim 9, wherein said intermediate point delimits said non-turbulent and turbulent zones, and said injection of cold reducing gas effects said admixture of said droplets and said particles.

13. A process according to claim 1, wherein said particles of heat carrier material of relatively large particles size are coke particles.

* * * * *